United States Patent
Sudin et al.

(10) Patent No.: US 9,561,121 B2
(45) Date of Patent: Feb. 7, 2017

(54) DEVICES AND METHODS FOR ASSISTING MEDICAL TREATMENTS

(71) Applicant: RAPID MEDICAL LTD., Yokneam (IL)

(72) Inventors: Yuri Sudin, Modiin (IL); Danel Mayer, Tel Aviv (IL); Ronen Eckhouse, Shimshit (IL)

(73) Assignee: RAPID MEDICAL LTD., Yokneam (IL)

(*) Notice: Subject to any disclaimer, the term of this patent is extended or adjusted under 35 U.S.C. 154(b) by 0 days.

(21) Appl. No.: 14/370,369

(22) PCT Filed: Jan. 3, 2013

(86) PCT No.: PCT/IB2013/000359
§ 371 (c)(1),
(2) Date: Jul. 2, 2014

(87) PCT Pub. No.: WO2013/102848
PCT Pub. Date: Jul. 11, 2013

(65) Prior Publication Data
US 2014/0343663 A1 Nov. 20, 2014

Related U.S. Application Data

(60) Provisional application No. 61/582,907, filed on Jan. 4, 2012, provisional application No. 61/637,349, filed
(Continued)

(51) Int. Cl.
*A61F 2/82* (2013.01)
*A61F 2/86* (2013.01)
(Continued)

(52) U.S. Cl.
CPC .............. *A61F 2/86* (2013.01); *A61B 17/1204* (2013.01); *A61B 17/12031* (2013.01);
(Continued)

(58) Field of Classification Search
CPC .............. A61M 29/02; A61B 17/12031; A61B 17/1204; A61B 17/12113; A61B 17/12177; A61B 2017/1205; A61B 2017/12054; A61F 2/86; A61F 2/95; A61F 2002/825; A61F 2002/9522
See application file for complete search history.

(56) References Cited

U.S. PATENT DOCUMENTS

| 5,897,567 A | 4/1999 | Ressemann et al. |
| 5,972,019 A | 10/1999 | Engelson et al. |
(Continued)

FOREIGN PATENT DOCUMENTS

| DE | 10 2008 038 195 | 2/2010 |
| DE | 10 2010 025 661 | 8/2011 |
(Continued)

OTHER PUBLICATIONS

International Search Report from the European Patent Office for International Application No. PCT/IB2013/000359, mailing date Jan. 7, 2014.
(Continued)

*Primary Examiner* — Julian W Woo
*Assistant Examiner* — Lucas Paez
(74) *Attorney, Agent, or Firm* — Finnegan, Henderson, Farabow, Garrett & Dunner, L.L.P.

(57) ABSTRACT

An intravascular device (100) includes an elongated shaft (3) extending in an axial direction and an expandable braided arrangement (110) of a plurality of filaments. The braided arrangement has a proximal end, a distal end (1), and an intermediate region therebetween. The intravascular device can include an endpiece (112-1) located proximate an intersection of the elongated shaft and the braided arrangement. The endpiece can be configured to orient the filaments in a substantially single file continuum. At a junction with
(Continued)

the endpiece, the filaments can initially extend in a substantially parallel, non-crossing manner, and as the filaments extend toward the intermediate region, the initially extending non-crossing filaments can cross each other.

14 Claims, 15 Drawing Sheets

Related U.S. Application Data on Apr. 24, 2012, provisional application No. 61/691,086, filed on Aug. 20, 2012.

(51) Int. Cl.
*A61M 29/02* (2006.01)
*A61B 17/12* (2006.01)

(52) U.S. Cl.
CPC .. *A61B 17/12113* (2013.01); *A61B 17/12177* (2013.01); *A61M 29/02* (2013.01); *A61B 2017/1205* (2013.01); *A61B 2017/12054* (2013.01); *A61F 2002/825* (2013.01)

(56) References Cited

U.S. PATENT DOCUMENTS

| | | | |
|---|---|---|---|
| 6,066,158 A | 5/2000 | Engelson et al. | |
| 6,346,116 B1 * | 2/2002 | Brooks | A61F 2/01 606/159 |
| 6,764,503 B1 * | 7/2004 | Ishimaru | A61F 2/07 606/108 |
| 2007/0203559 A1 * | 8/2007 | Freudenthal | A61B 17/22 623/1.3 |
| 2011/0009941 A1 | 1/2011 | Grandfield et al. | |
| 2011/0046716 A1 | 2/2011 | Parkinson et al. | |
| 2011/0054504 A1 | 3/2011 | Porter | |
| 2011/0288572 A1 * | 11/2011 | Martin | A61B 17/221 606/159 |

FOREIGN PATENT DOCUMENTS

| | | |
|---|---|---|
| JP | H10 151136 A | 6/1998 |
| JP | 2011 512206 A | 4/2011 |
| WO | WO 01/15629 | 3/2001 |
| WO | WO 2008/156468 | 12/2008 |
| WO | WO 2009/105710 | 8/2009 |
| WO | WO 2010/120926 A1 | 10/2010 |

OTHER PUBLICATIONS

Written Opinion of the International Searching Authority from the European Patent Office for International Application No. PCT/IB2013/000359, mailing date Jan. 7, 2014.
Office Action dated Sep. 26, 2016, issued in counterpart Japanese Patent Application No. 2014-550782, 5 pages.

* cited by examiner

SECTION B-B
500
502

SECTION A-A
502
500

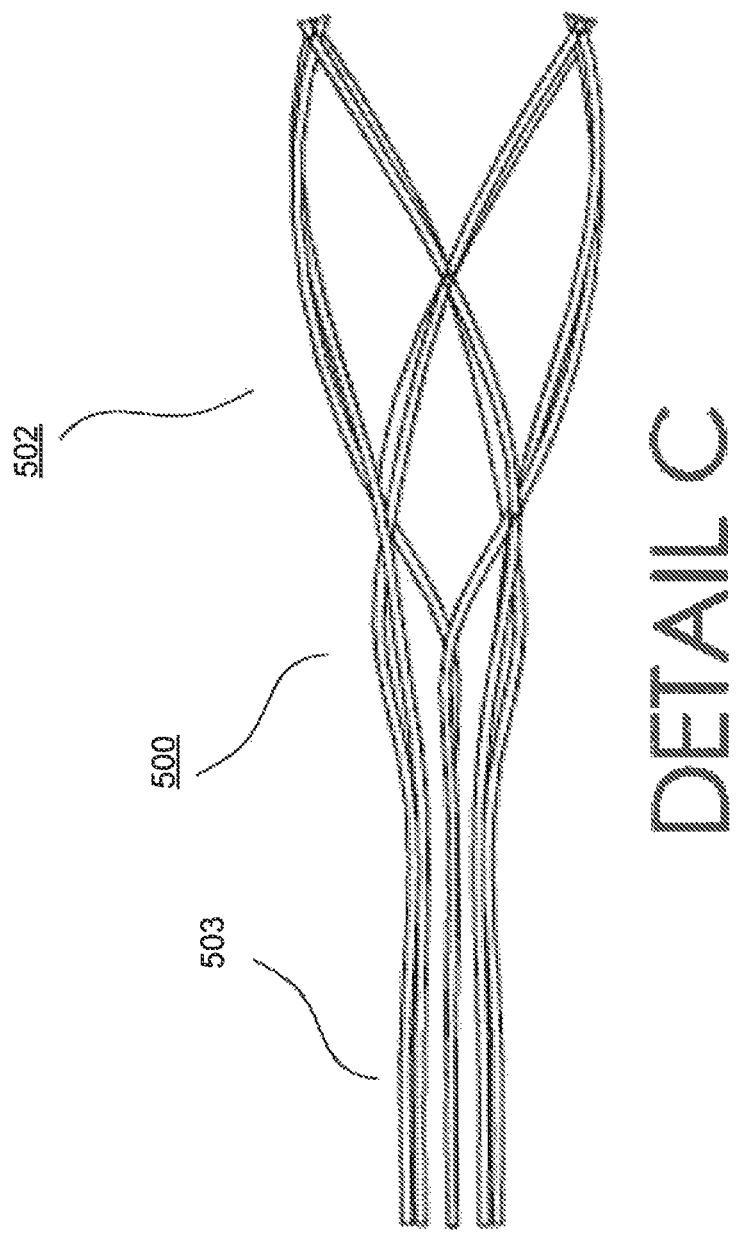

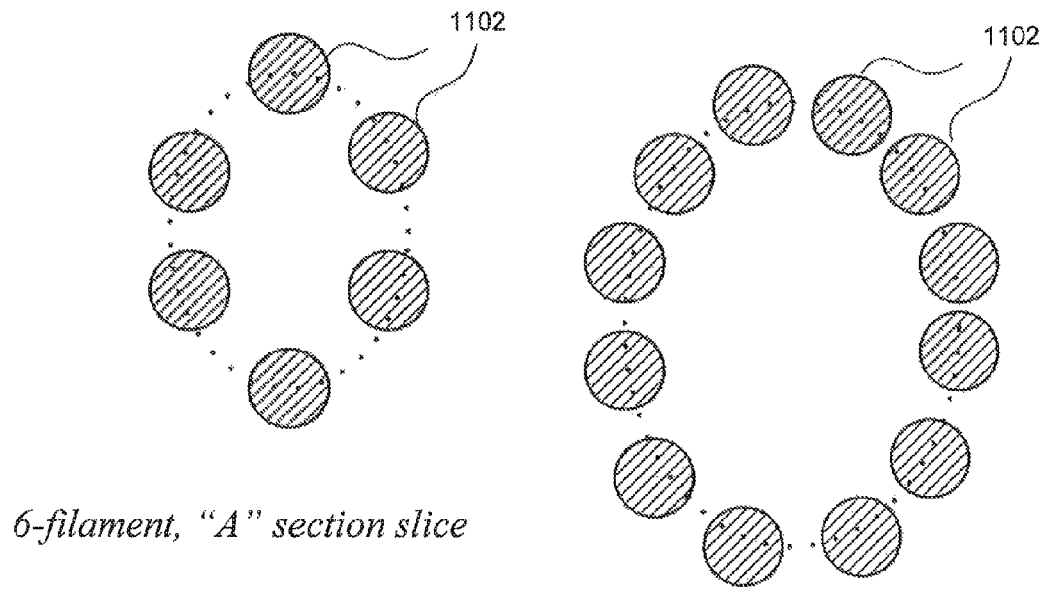
*6-filament, "A" section slice*
FIG. 11A
*12-filament, "A" section slice*
FIG. 11B
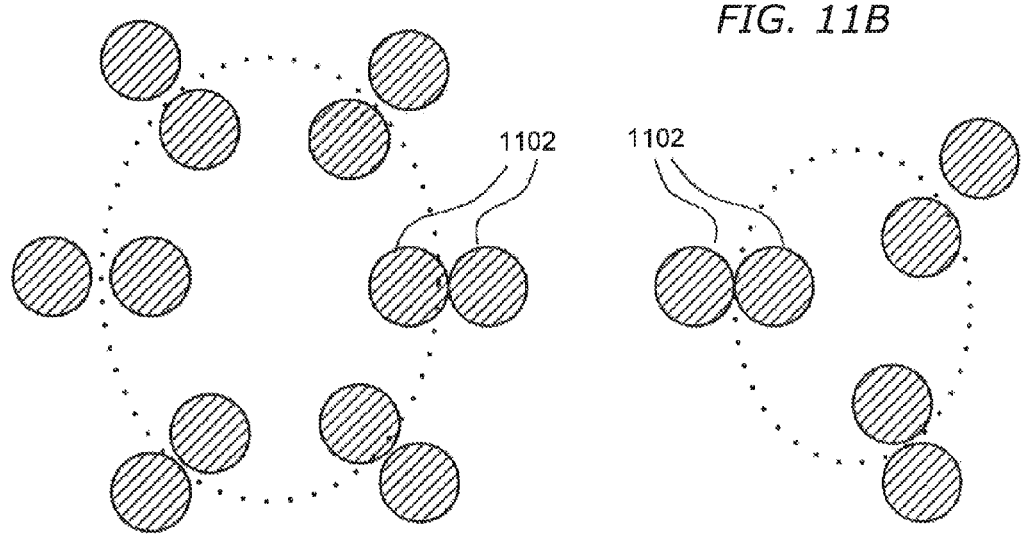
*12-filament, "B" section slice*
FIG. 11D
*6-filament, "B" section slice*
FIG. 11C

DEVICES AND METHODS FOR ASSISTING MEDICAL TREATMENTS

PRIORITY

This application claims the benefit of priority from: U.S. Provisional Application No. 61/582,907 filed Jan. 4, 2012, U.S. Provisional Application No. 61/637,349 filed Apr. 24, 2012, and U.S. Provisional Application No. 61/691,086, filed Aug. 20, 2012, the disclosures of all of which are herein incorporated by reference in their entirety.

BACKGROUND

An aneurysm is an abnormal local dilatation in the wall of a blood vessel, usually an artery, due to a defect, disease, or injury. One type of aneurysm is an intracranial aneurysm (IA). IAs have a risk of rupturing, which can result in a subarachnoid hemorrhage, a serious medical condition, often leading to severe neurological deficit or death.

A treatment goal of IAs is the prevention of rupture. Treatment methods can include two intervention options: clipping of the aneurysm neck and endovascular methods such as coiling and flow diversion. Traditionally, surgical clipping has been the treatment modality of choice for both ruptured and unruptured IAs; however, since the introduction of controlled detachable coils (GDC) for packing of aneurysms, endovascular aneurysm therapy has become an acceptable alternative to conventional neurosurgical treatment.

The technique of standard coil embolization can be limited by the shape of some of these aneurysms. For example, wide-necked aneurysms can be difficult to treat because of their unfavorable geometry, which can reduce the possibility of achieving dense packing and elimination of the aneurysm from circulation. One risk is the possibility of coil herniation through the broad neck into the parent vessel. This can cause thromboembolic events, which can be the most frequent and serious complications associated with endovascular treatment of intracranial aneurysms, Various adjunctive techniques have been developed for the treatment of large, wide-neck and other complicated aneurysms. One technique is balloon-assisted treatment, in which a balloon is temporarily inflated across the aneurysm neck during coil insertion. In recent years, stents for intracranial use have become available, first as balloon-mounted stents and later as self-expandable stents with an open-cell or closed-cell design.

SUMMARY

In an aspect, an intravascular device consistent with this disclosure can include an elongated shaft extending in an axial direction and an expandable braided arrangement of a plurality of filaments. The intravascular device can include an endpiece located proximate an intersection of the elongated shaft and the braided arrangement. The braided arrangement can have a proximal end, a distal end, and an intermediate region therebetween. Further, the endpiece can be configured to orient the filaments in a substantially single file continuum. At a junction with the endpiece, the filaments can initially extend in a substantially parallel, non-crossing manner, and as the filaments extend toward the intermediate region, the initially extending non-crossing filaments can cross each other.

Consistent with a further aspect of this disclosure, an intravascular device can include an elongated shaft extending in an axial direction, where the elongated shaft is formed of a plurality of filaments. The intravascular device can also include an expandable braided arrangement of the plurality of filaments, where the braided arrangement can have a proximal end, a distal end, and an intermediate region therebetween. In an aspect, the intravascular device can also include a transition region of the plurality of filaments at an intersection of the elongated shaft and the braided arrangement, where the plurality of filaments on one side of the transition region are oriented in a substantially parallel, non-crossing manner, and the plurality of filaments on an opposing side of the transition region cross each other

BRIEF DESCRIPTION OF THE DRAWINGS

FIG. 6C depicts a detail of the embodiment of FIG. 5 near a proximal end of the expandable member;

FIG. 11A-D depicts filament arrangements for 6-filament and 12-filament devices along selected planes;

DESCRIPTION OF EXEMPLARY EMBODIMENTS

Embodiments of the present disclosure provide devices for assisting medical treatments (for example, and without limitation, assisting endovascular treatment of aneurysm and binary tract treatment). In addition, embodiments of the described devices can also be used as a temporary scaffold for vessel protection during surgery, to remove clots from blood vessels and cross occluded sections of vessels. Further embodiments of described devices can also be used to treat vessel vasospasm and to expand other endovascular devices.

Figure 1:
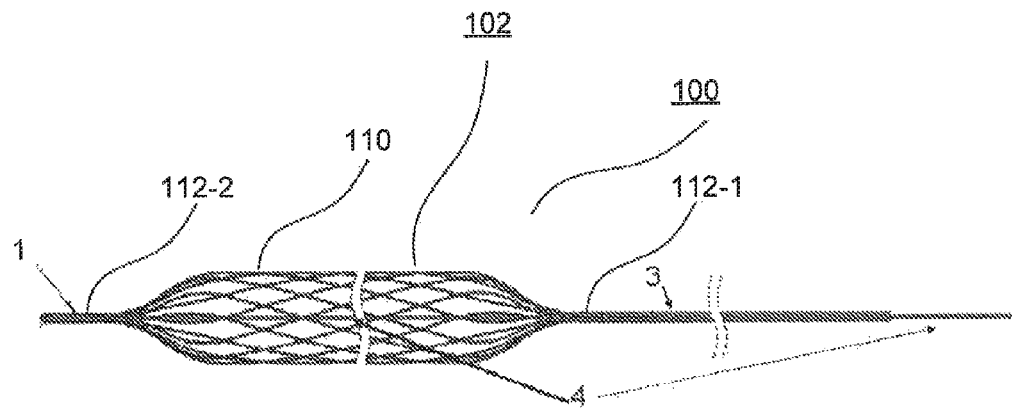
FIG. 1 is a perspective view of an embodiment of a device consistent with the disclosure exhibiting an expandable member and a control filament in a shaft.
Figure 2:
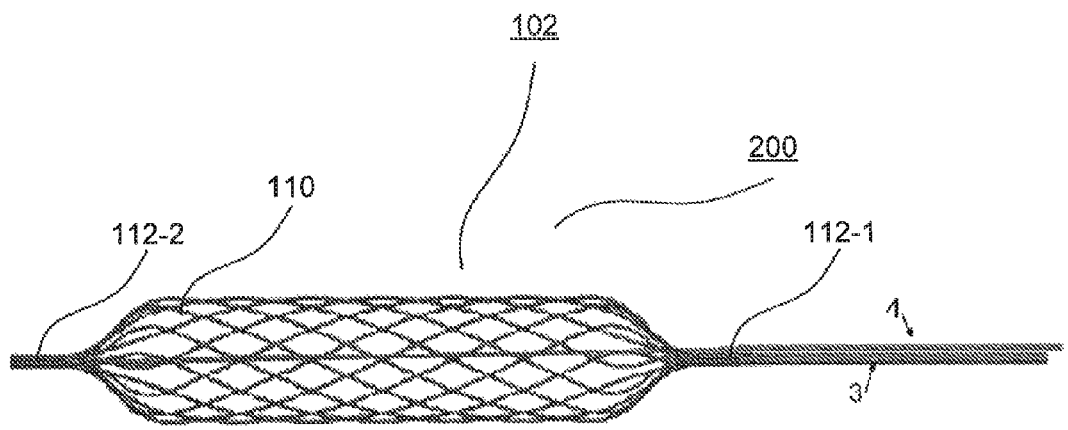
FIG. 2 is a perspective view of further embodiment consistent with the disclosure exhibiting an expandable member and a control filament outside a shaft.

A device 100 consistent with the present disclosure is depicted in FIG. I. The device 100 can include an expandable member 110 that can be mounted on a shaft 3. As used herein, an expandable member can be any known mechanically expandable device, and can include a mesh, a balloon, or any other mechanical structure. Moreover, the expandable member can be made of any material that allows for expansion and contraction and can be any structure capable of selective and variable expansion, contraction and density in response to applied forces. For example, when a force is exerted on a portion of the expandable member 110 in one direction (such as a force on a distal endpiece 112-2 connected to the expandable member 110), the expandable member 110 can be configured to expand. As depicted in FIGS. 1 and 2, the expandable member 110 can be configured to exhibit a substantially uniform shape when it expands.

Figure 3:
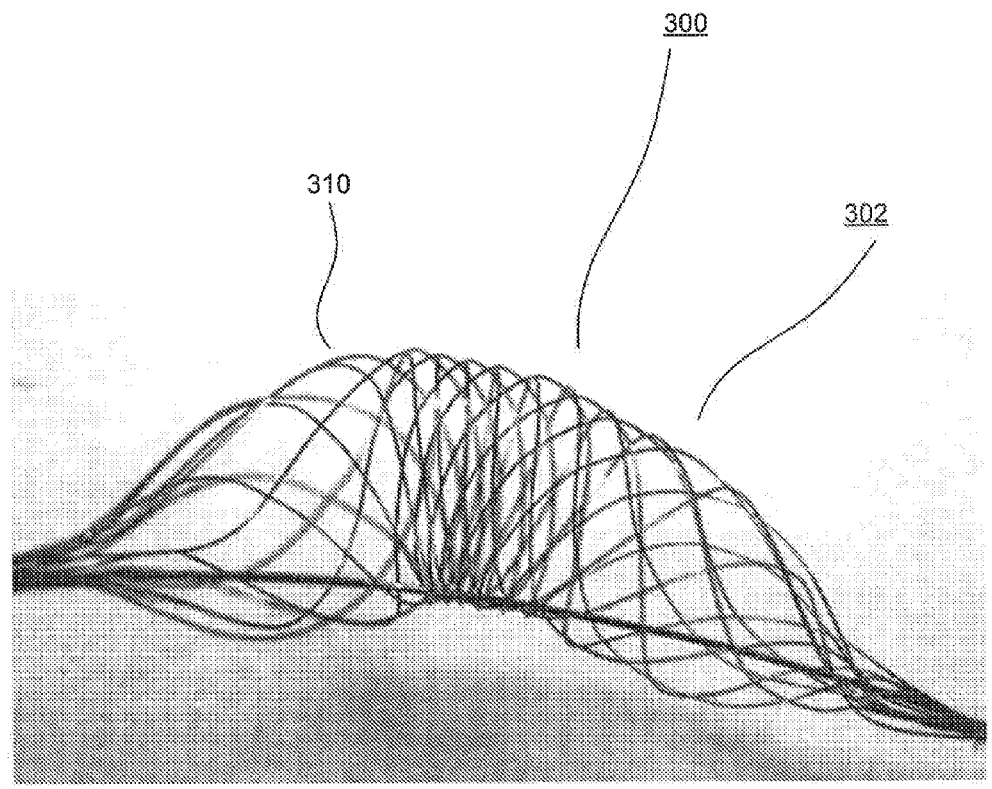
FIG. 3 is a perspective view of an embodiment exhibiting an expandable member with an asymmetrical shape.

Alternatively, as depicted in FIG. 3, an expandable member 310 (as part of a device 300) can also be configured to exhibit a substantially asymmetrical shape when it expands. Consistent with the disclosure, an asymmetrical shape can improve an embodiment's ability to comply to the anatomy of a blood vessel. When a force is exerted on the portion of the expandable members in another direction (e.g., in a direction opposite the direction configured to cause expansion of expandable members), the expandable member can be configured to contract. According to another embodiment of the device, the expandable member can be configured to achieve higher wire density within portions of the expandable member in the device. In the embodiment shown in FIG. 1, for example, the expandable member 110 can include a filament mesh 102, where the filament material in the mesh can be wire.

In the embodiment shown in FIG. 1, a distal endpiece 112-2 of the expandable member 110 can be connected to a distal end 1 of an elongated control member 4 which can extend from a distal end of a shaft 3. As used herein the term "connected" means linking, bringing, and/or joining together by any type of mechanical connection.

In some embodiments the distal end 1 can be designed to be atraumatic to a blood vessel. For example, as illustrated in FIG. 1, the distal end 1 can be connected to an elongated, radio-opaque soft wire (such as guide wire tip). In another embodiment, a distal endpiece can reside inside the elongate body of the device, thereby eliminating the need for the elongated control member 4 to extend completely through the elongate body. In such an embodiment, a distal end of the device can resemble the branch connection point of an apple. The elongated control members can be any elongated structures capable of exerting a force on an endpiece 112-2 of the expandable member 110. According to some embodiments, the elongated control members can be connected to a portion of the expandable member of the device, and can maintain the connection to the portion while undergoing pushing and pulling forces. Alternatively, the elongated control members can extend beyond the distal endpiece 112-2.

The elongated control members can be wholly or partially flexible, hollow and/or solid. Accordingly, the elongated control members can include, but are not limited to, any filament, such as a shaft, a wire, or a rod. In an embodiment consistent with the disclosure, and as depicted for example in FIG. 1, the elongated control member 4 can be in the form of a wire.

In addition to the elongated control members, the treatment device can also include ex-vivo elements such as an insertion tool, a torquer, and a luer, one or more control handles.

As depicted in the figures, the elongated control members can be configured to reside within the shaft. For example, in FIG. 1 a proximal endpiece 112-1 connected to the expandable member 110 can be connected to a distal end of the shaft 3. In addition, the elongated control members 4 can extend through the center of the expandable member 110 and proximally inside the shaft 3. A further device—device 200 consistent with the present disclosure—is depicted in FIG. 2. The device 200 can include an expandable member 110 that can be mounted on a shaft 3 as described above in connection with FIG. 1. As is also consistent with the current disclosure, the elongated control member 4 in device 200 can be configured to be parallel to the shaft 3 rather than within shaft 3. That is, in device 200, the elongated control members 4 can extend outside of the shaft 3 in a direction that is parallel to the longitudinal axis of the shaft 3.

While the preceding discussion referred to the embodiments depicted in FIG, 1 and FIG. 2, it is understood that it also can apply to other embodiments, such as (without limitation) device 300 of FIG. 3.

The elongated control members can be configured to control the expansion of the treatment device at the target vessel. When the elongated control member undergoes a pulling force in a proximal direction relative to the shaft, a diameter of the expandable member can be enlarged to exhibit a substantially uniform shape (or an asymmetrical shape) between the proximal end and the distal end of the expandable member. This can facilitate vessel compliance and adherence to the vessel wall. When the elongated control members undergo a pushing force, an outer diameter of the expandable member can be diminished, and the elongate member can be readily delivered to a treatment site or retrieved from treatment site. This control of the diameter of the expandable member at treatment sites can allow an operator of the device 100 (or any other devices illustrated in the figures) to perform gentle reposition maneuvers and/or can allow an operator to dislodge a coil ending if engaged in one of the cells.

As aforementioned, the elongated control member can also be configured to control other properties of at least one portion of the expandable member. For example, the elongated control member can be configured to control the wire density of the treatment device at the target vessel. If the elongated control member undergoes a pulling force in a proximal direction relative to the shaft, a wire density of the expandable member can be made higher.

Figure 4A:
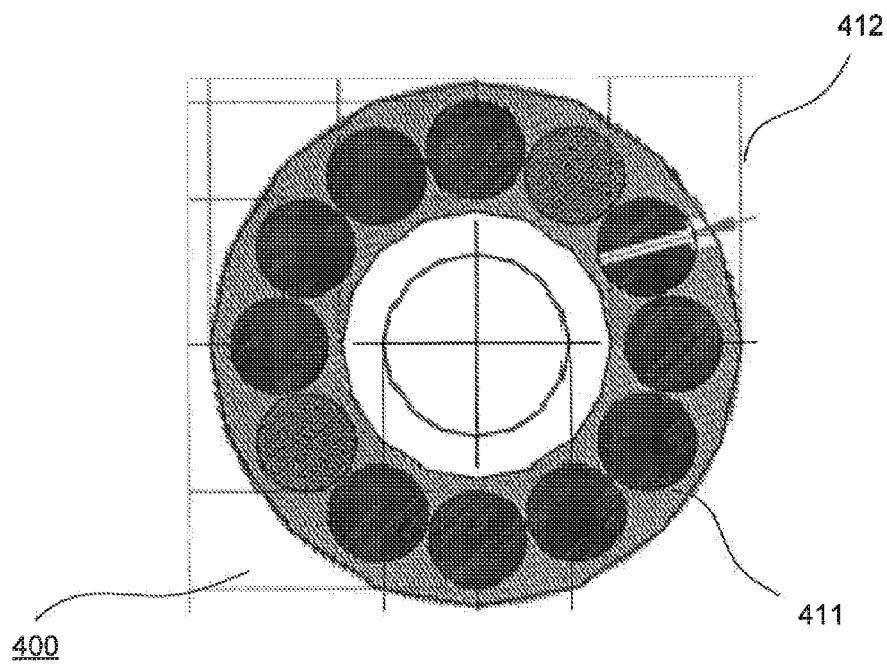
FIG. 4A is a perspective view of an endpiece consistent with the present disclosure.

In FIG. 4A an endpiece 412 consistent with the disclosure is depicted. Apertures 411, which can accommodate the filaments that make up the mesh of the expandable member (such as wire) are shown in a cylindrical arrangement.

When the device according to any of the embodiments is used in the human neurovasculature, it can be flexible and have a small form factor. In general, neurovascular devices can be configured to be delivered through supple microcatheters which have a small internal diameter of about 0.5 mm. As a result, an exemplary device of the present disclosure can be configured to have a minimal outer diameter when collapsed during delivery.

Figure 4B:
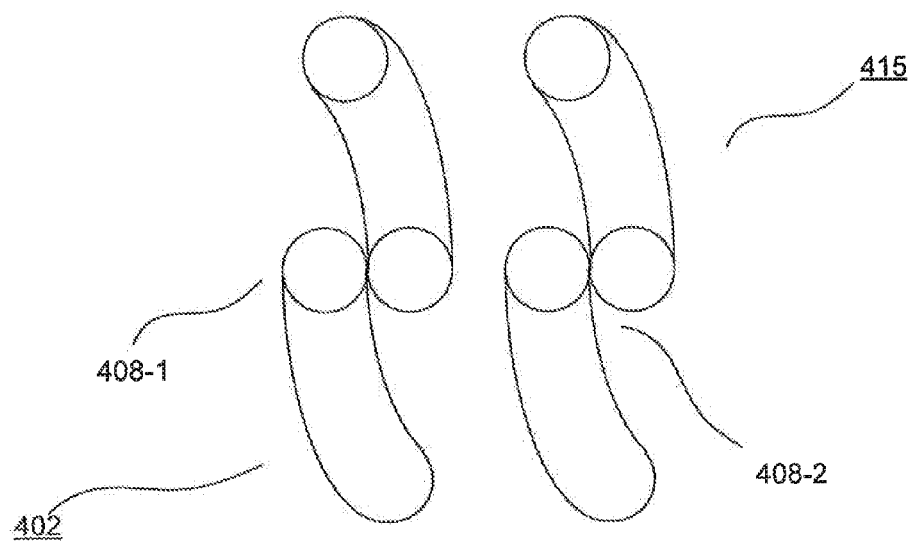
FIG. 4B is a perspective view of a cross section of a contracted expandable member in an intermediate region.

For example, the expandable member according to any of the embodiments can be configured to have a minimum profile. Consistent with the disclosure, there can be filament crossings at an intermediate region of the filament mesh of the expandable member. That is, in an embodiment consistent with the disclosure, the diameters of four filaments can be considered in determining a minimum outer diameter of the expandable member when the device is sheathed. More specifically, in an embodiment depicted in FIG. 4B, a first crossing point 408-1 of two filaments of a filament mesh (such as filament mesh 102 in FIG. 1) on one portion of the expandable member cannot be smaller than the diameter of two filaments that cross at the first crossing point 408-1. In a minimum configuration, and due to the symmetry of the expandable member, there can be a second crossing point 408-2 diametrically opposite the first crossing point 408-1, and subject to the same minimal thickness. Accordingly, a minimum thickness of the filament mesh of the expandable member when collapsed can be expected to be determined by the thickness of four filaments diameters (a configuration 415 depicted in FIG. 4B). This can occur in an intermediate region of the expandable member (i.e., the region between a proximal region of the expandable member near a proximal endpiece and a distal region of the expandable member near a distal endpiece).

Figure 4C:
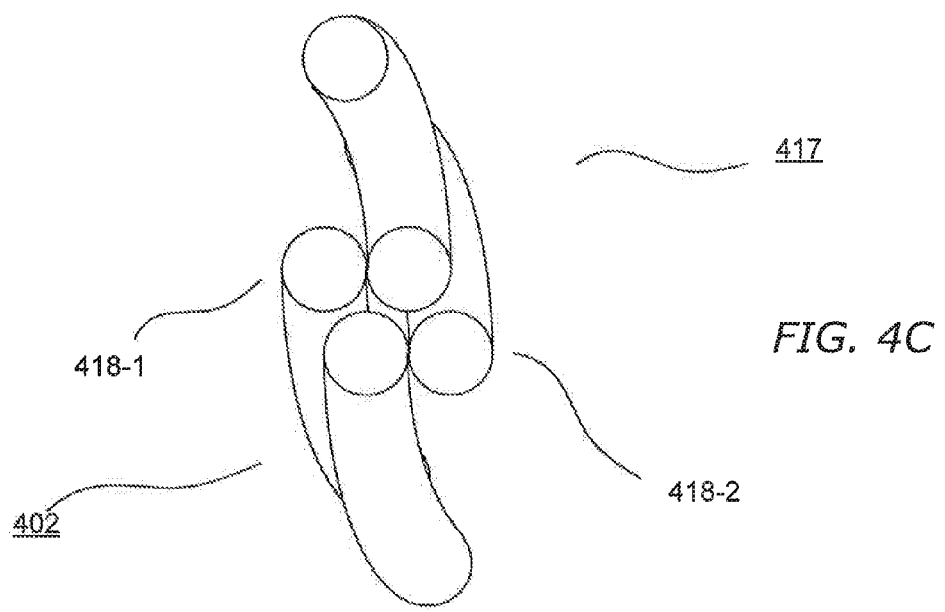
FIG. 4C is a perspective view of a cross section of a contracted expandable member where filaments can be ordered near a proximal end or a distal end of the expandable member.

Nonetheless near a proximal endpiece, (and in some embodiments a distal endpiece), the filaments that make up the filament mesh can be ordered one on the side of the other such that a minimal outer diameter of the expandable member is determined by only two filaments (rather than four). This ordered arrangement, when the filament mesh is collapsed, is depicted in FIG. 4C—which depicts a first crossing point 418-1 that can be adjacent a second crossing point 418-2. As a result of the configuration 417 depicted in FIG. 4C, the total diameter of the filament mesh, when collapsed, can be minimal.

Figure 4D:
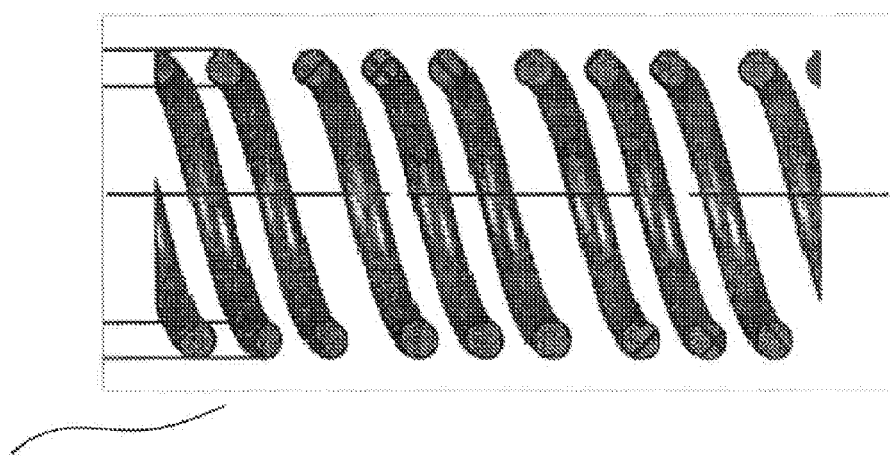
FIG. 4D is a perspective view of a coiled filament arrangement near a proximal end or a distal end of an expandable member.

Alternatively, the filaments that make up the filament mesh can be coiled at the proximal and distal ends of the expandable member, as in configuration 419 depicted in FIG. 4D, to achieve a similar effect. When the filaments are coiled opposite a filament mesh region, an endpiece may not be necessary to transition a plurality of filaments from a shaft region of a device to a proximal region of the expandable member.

Figure 5:
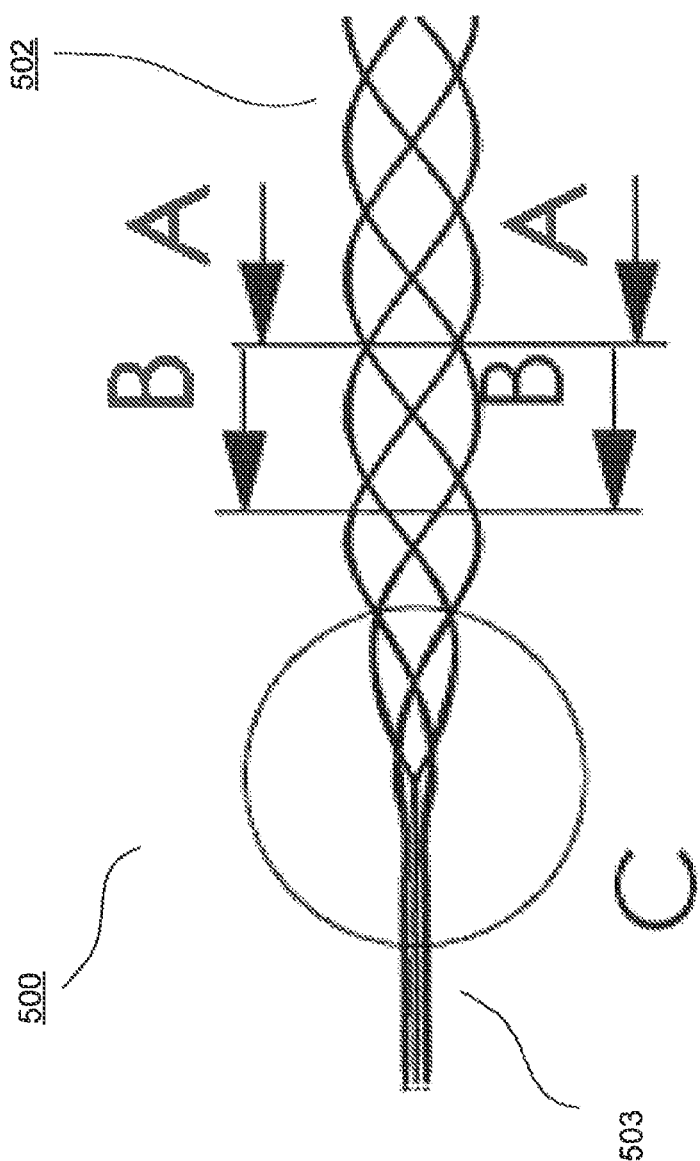
FIG. 5 depicts an embodiment consistent with the disclosure utilizing eight filaments, where the filaments are parallel to a shaft axis in the region of the shaft.

In an embodiment consistent with the disclosure a filament arrangement 500, as depicted in FIG. 5, can be utilized. The embodiment disclosed in FIG. 5 depicts eight filaments transitioning from a shaft region 503 to a filament mesh 502. In the shaft region 503, the eight filaments are depicted as oriented parallel to a shaft axis.

Figure 6B:
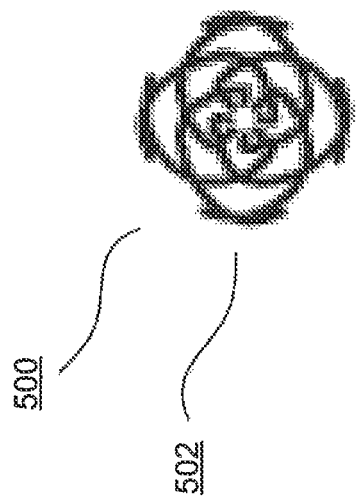
FIGS. 6A-B depict perspective views of the embodiment of FIG. 5 along selected planes.
Figure 6A:
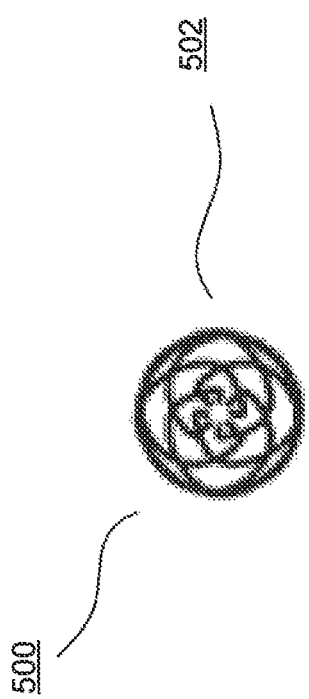

FIG. 6A depicts a view along a cross section of the filament arrangement 500, and depicts eight filaments forming a filament mesh 502 from a minimal diameter. FIG. 6B depicts a view parallel to the view of FIG. 6A, but closer to the transition region from the shaft region 503. FIG. 6C depicts further detail of eight filaments transitioning from a shaft region 503 to a filament mesh 502. In the depicted embodiments of FIGS. 5 and 6A-C, there is no endpiece shown (such as the endpiece 412 of FIG. 4A). Among other things, where the filaments that make up the filament mesh transition from an orientation that is parallel to a shaft axis in a shaft region to a filament mesh, the use of an endpiece can maintain the arrangement of filaments to ensure that a minimal cross section is presented near the endpiece while still maintaining a hollow center region through which an elongated control member may reside.

Figure 7:
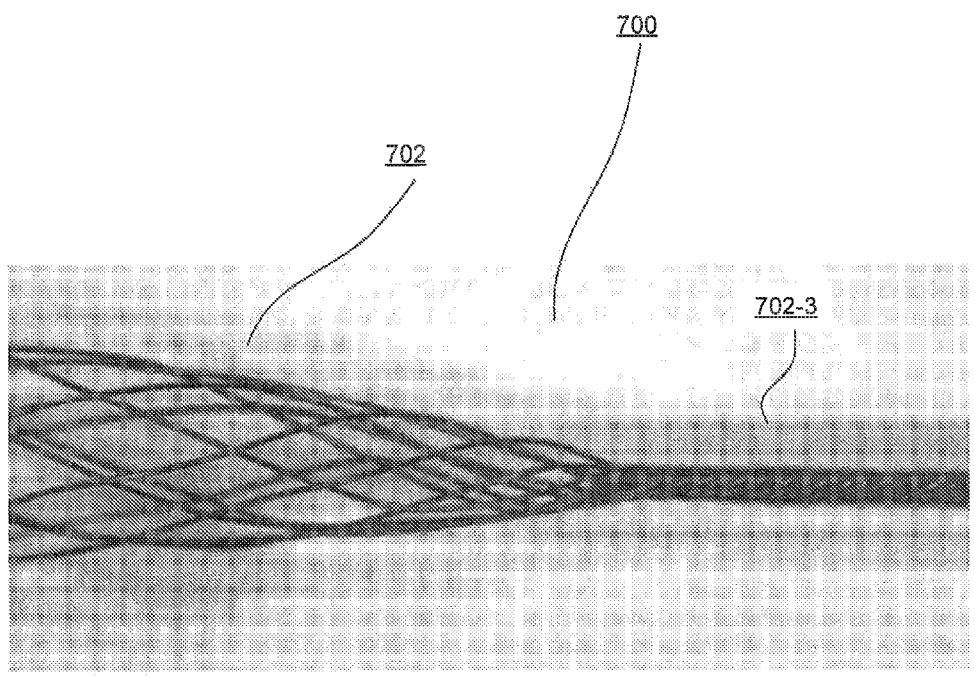
FIG. 7 depicts an embodiment consistent with the disclosure utilizing twelve filaments, where the filaments are coiled around a shaft axis in the region of the shaft.

In another embodiment consistent with the disclosure, a filament arrangement 700, as depicted in FIG. 7, can be utilized. The embodiment disclosed in FIG. 7 depicts twelve filaments transitioning from a shaft region 702-3 to a filament mesh 702. In the shaft region 702-3, the 12 filaments are coiled about a shaft axis. For the embodiment shown in FIG. 7, the use of an endpiece can be optional.

Figure 8:
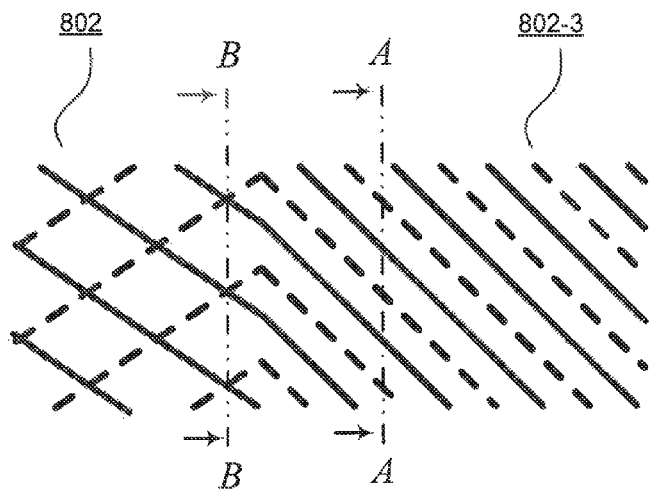
FIG. 8 is a diagram indicating an arrangement of filaments consistent with the disclosure in a region transitioning from a shaft region to a proximal end of an expandable member without an endpiece.
Figure 9:
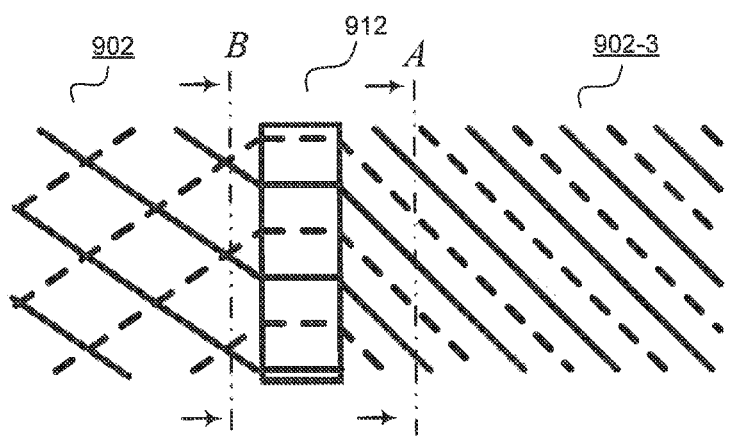
FIG. 9 is a diagram indicating an arrangement of filaments consistent with the disclosure in a region transitioning from a shaft region to a proximal end of the expandable member with an endpiece.
Figure 10:
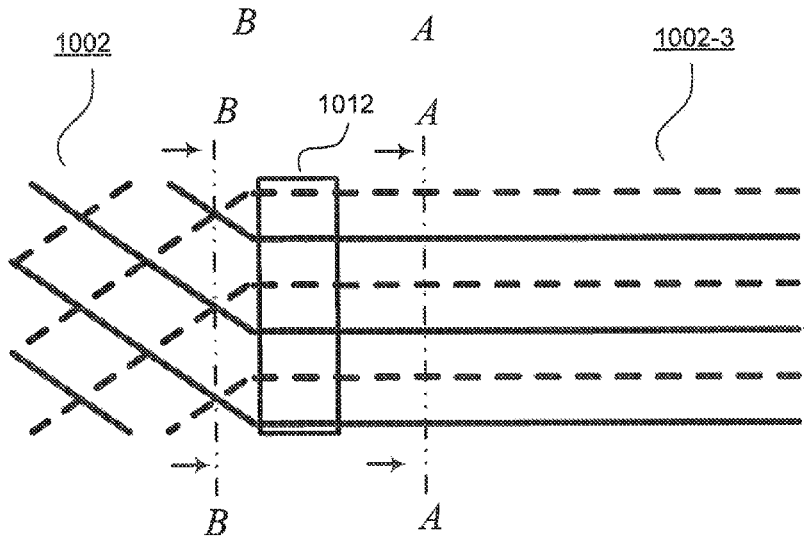
FIG. 10 is a diagram indicating another arrangement of filaments consistent with the disclosure in a region transitioning from a shaft region to a proximal end of the expandable member with an endpiece.

FIGS. 8-10 provide diagrams indicating arrangement of filaments consistent with the disclosure in a region transitioning from a shaft region to a proximal end of the expandable member. For purposes of clarity only, the alternating filaments that make up the filament mesh in FIGS. 8-10 are shown as either solid lines or dashed lines. The arrangement depicted in FIG. 8 is similar to that depicted in FIG. 7, and shows a transition from a series of coiled filaments (in shaft region 802-3) to a filament mesh 802. In FIG. 8, there is no endpiece depicted.

The arrangement depicted in FIG. 9 is also similar to that depicted in FIG. 7, and shows a transition from a series of coiled filaments (in shaft region 902-3) to a filament mesh 902. In FIG. 9, there is depicted an endpiece 912, which can be used to maintain the coil in shaft region 902-3 while the mesh in the filament mesh 902 expands or contracts under control of an elongated control member (not shown).

The arrangement depicted in FIG. 10 is similar to that depicted in FIGS. 5 and 6A-C, and shows a transition from a series of parallel filaments (in shaft region 1002-3) to a filament mesh 1002. In FIG. 10, there is also depicted an endpiece 1012, which can be used to maintain the arrangement of the filaments in the shaft region 1002-3 while the mesh in the filament mesh 1002 expands or contracts under control of an elongated control member (not shown).

FIGS. 8-10 also include lines indicating a plane "A" (which is in a shaft region) and a plane "B" (which is in a filament mesh region), The plane "B" is selected to pass through the filament mesh region at a point where filaments cross.

Consistent with the disclosure, FIGS. 11A-D depict exemplary "slices" along plane "A" and plane "B" for a six-filament arrangement (FIGS. 11A and 11C) and for a twelve-filament arrangement (FIGS. 11B and 11D).

FIGS. 11A and 11B depict an arrangement of filaments 1102 that are in a single-file continuum about an axis. That is, as used herein, a single-file continuum of filaments about an axis means filaments arranged such that the filament cross-sections lie one after another in a loop about the axis, without the filament cross-sections lying in a substantially stacked configuration relative to the axis, Moreover, a "loop" means any simple closed curve or a combination of lines and curves that connects to itself, such as a circle, oval, square, rectangle, triangle, etc. In contrast, FIGS. 11B and 11D depict an arrangement of filaments 1102 that are not in a single-file continuum about an axis, but are in a substantially stacked configuration near and at filament crossing points. Further still, filaments arranged in a single-file continuum that are adjacent to one another may touch one another or they may not. For example, two adjacent filaments as part of a single-file continuum arrangement can be spaced apart from one another.

Moreover, although the endpiece 412 shown in FIG. 4A depicts apertures in a one-to-one relationship with filaments, one of ordinary skill in the art would appreciate that an endpiece consistent with this disclosure can include one or more channels (each channel of which can accomodate several filaments in a single-file continuum configuration) rather than the configuration of apertures of endpiece 412.

Figure 12:
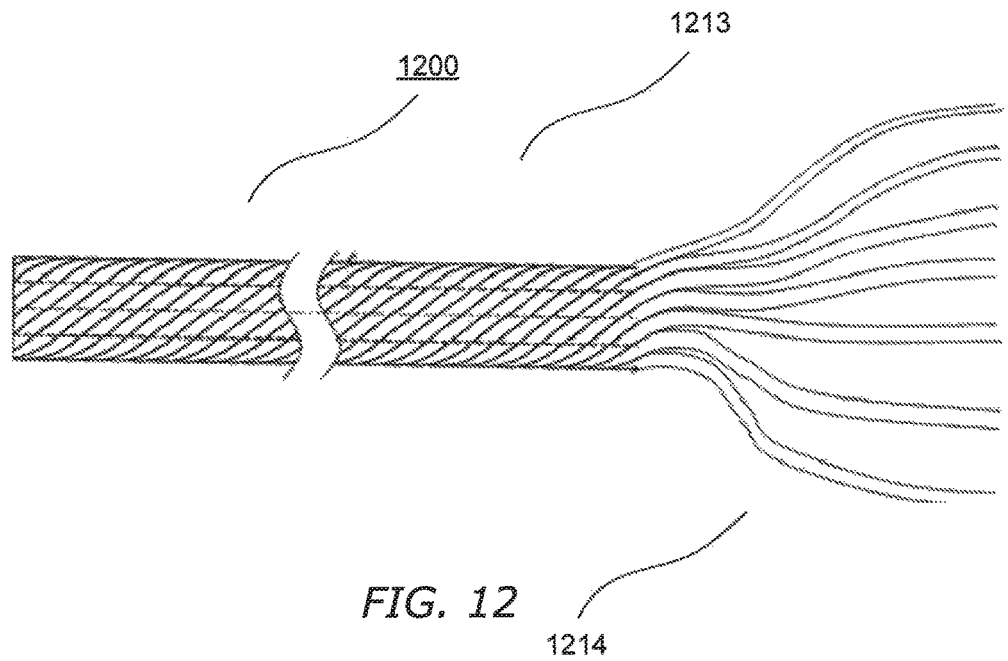
FIG. 12 is a perspective view of a device for treatment with a shaft including a hollow torque cable tube in a wound and unwound state.

Further still, as depicted in FIG. 12 (and similar to the embodiments of FIGS. 7 and 8), a device consistent with this disclosure can be configured to provide a minimal profile by including a hollow torque cable 1200, which includes a wound portion 1213 and an unwound portion 1214. By way of example only, the shaft 3 of FIGS. 1 and 2 can include the wound portion 1213 of the hollow torque cable 1200, and the expandable member can be configured from the wires of the hollow torque cable 1200 in the unwound portion 1214. Such a configuration can exhibit an optimal profile because no additional connecting media (such as endpiece 412 depicted in FIG. 4A) is required. In any of the embodiments discussed here, however, (including without limitation all of the embodiments depicted in FIGS. 5-12) a shaft and an expandable member can also be welded or soldered together consistent with the disclosure, and can achieve minimal profile. The shaft can be welded or soldered to the expandle member with or without the use of an endpiece. Further still, a shall and an expandable member can be connected using a heated polymer or glue to bond the filaments. Returning to FIG. 12, FIG. 12 depicts the transition from the wound portion 1213 of the hollow torque cable 1200 to the unwound portion 1214. According to some embodiments the dimensions and construction of the wires can be also determined by the dimensions of the neurovascular microcatheter described above. The diameter of the some of the wires described above can be between 50 μm and 120 μm (e.g. 75 μm). The dimensions of the elongated control members can be smaller than 50 μm (e.g. 25 μm or 10 μm).

Further still, a device with the specified filament arrangements (as depicted in FIGS. 5-12) on only the proximal or distal region of the expandable member is also consistent with this disclosure. By the way of example only, a device can have an expandable member with an open distal end. The filaments of the expandable member can be connected as described above to the shaft at the proximal end but can be looped back at the distal without being closed or connected again. In yet another example, the filaments \at the distal end can be connected together without arranging them in the low profile arrangement described herein.

The expandable member can be made of any suitable flexible material known to those skilled in the art. Suitable expandable materials can include, but is not limited to, polymers, metals, metal alloys, and combinations therefore. In an embodiment, for example, the expandable member can be constructed from super elastic metals such as Nitinol with minimal outer diameter. In order to visualize the expandable member with angiographic imaging, the expandable member can further include a radio-opaque marker and/or material. For example, in an embodiment, the expandable member can include a plurality of Nitinol wires with a core made of Tantalum or Platinum metals. The radiopaque core can be 20% to 50% by volume (e.g. 30% or 40%).

Figure 13:
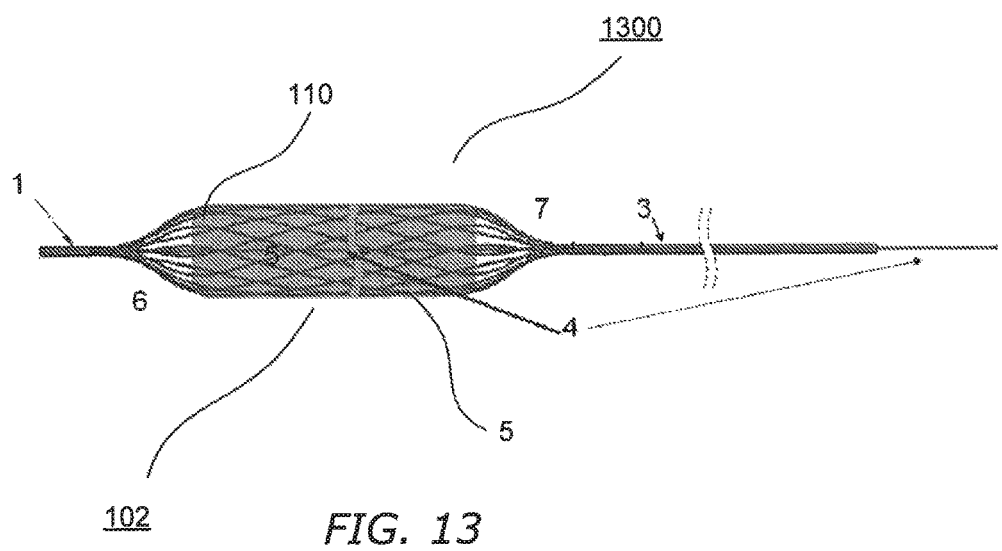
FIG. 13 is a perspective view of a further embodiment consistent with the disclosure.

The device according to any of the embodiment in the figures for treating a medical condition (e.g., an aneurysm or biliary tract) can further be configured to reduce the risk of coil herniation into the parent vessel. For example, in an embodiment, the size of the cells (i.e., the spaces within the filament mesh 2 of the expandable member) which are aligned to the vessel wall can be minimal. On the other hand, as illustrated in FIG. 13 to allow continuous blood flow during operation, a proximal cell 7 and a distal cell 6 can be relatively large. Therefore the filament mesh 2 can be configured to exhibit different cell sizes and shapes. For example, the density of the cylindrical area which is aligned to the vessel wall can be 3 to 12 crossings per centimeter while the density of transition and conical area (the proximal and distal portion) can be 1 to 5 crossings per centimeter. As described above, the elongated control members can control the mentioned cell size and density of the expanded member. Using the elongated control members a variable cell size can be achieved. Consistent with a further embodiment, the filament mesh 2 can be configured to exhibit a relatively large concentration of filaments in the portion of the device that is facing the aneurysm neck. In yet another embodiment the aneurysm facing portion (which can be cylindrical) can be constructed of wound filaments. In one embodiment the spacing between the windings of the wound filaments can be controlled using a control filament associated with an elongated controlled member.

In yet another embodiment depicted in FIG. 13 as a device 1300, a main body 5 of the cell structure of the expandable member 110 can be covered completely or partially to achieve full blockage of the aneurysm neck. The covering of the cell structure of the expandable member can be achieved by using a variety of medical grade polymers, such as polyurethane, silicone etc. The covering of the cell structure of the expandable member can also be achieved with organic tissue such as Pericardium. This option can provide assistance in the case of a ruptured aneurysm, because the physician can block the aneurysm until it is embolized. While not depicted, a main body of the cell structure of the expandable member 310 in FIG. 3 can also be covered completely or partially to achieve full blockage of the aneurysm neck. In a further embodiment consistent with the disclosure, a method to block a ruptured aneurysm can include providing a pulling force an elongated control member 4 until the filament mesh 2 exhibits cells sufficiently small so as to substantially prevent blood flow into the aneurysm. In addition, the filaments of the filament mesh 2, the covering over the main body 5, or both can be configured to be drug eluting during the use of the device 1300. Moreover, the filaments of the filament mesh 2 can be covered with materials which expand upon interaction with liquids (for instance, hydrogels).

Figure 14:
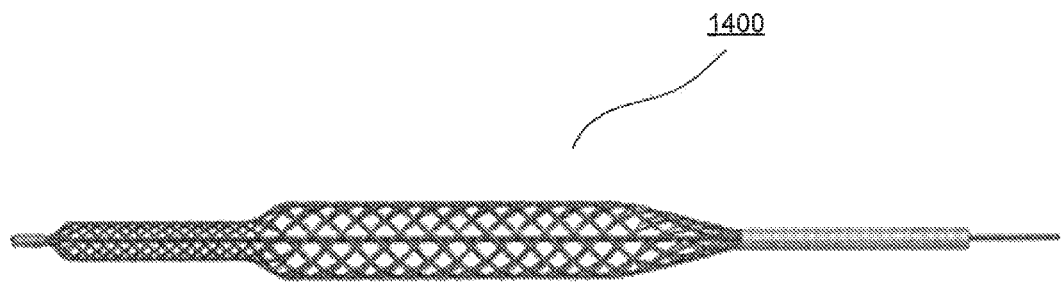
FIG. 14 is a perspective view of another embodiment consistent with the disclosure, including an expandable member exhibiting at least two substantially uniform shapes between its proximal end and its distal end.

In a further embodiment, a device consistent with this disclosure can be configured to address the clinical needs of the aneurysm coiling procedure. Because aneurysms usually occur at bifurcations and branches of arteries, the shape of the device can be configured to achieve improved vessel compliance at these anatomies. For example, the device 1400, depicted in FIG. 14, can be configured to exhibit at least two substantially uniform shapes between a proximal end and a distal end of the expandable member in the expanded configuration. Further still, the device 300, depicted in FIG. 3 can be configured to exhibit at least two asymmetrical shapes between the proximal end and the distal end of the expandable member 310, or at least an asymmetrical shape with another uniform shape. For example, a combination of shapes can include a pear-shape which can be used for treating endovascular aneurysms.

Figure 15:
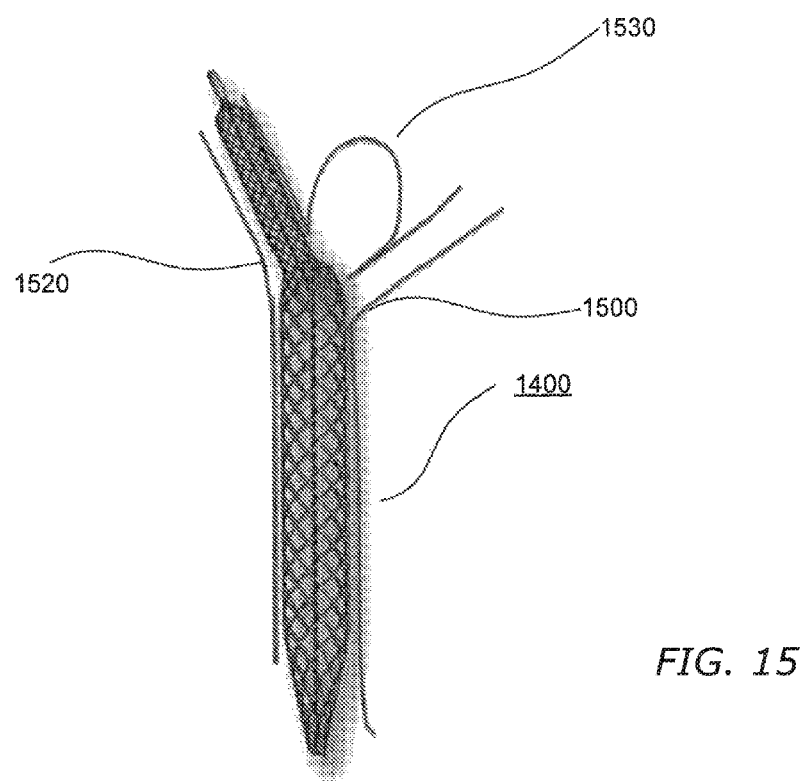
FIG. 15 is a perspective view of the device of FIG. 14 in a bifurcated vessel.

In the embodiment, depicted in FIG. 15, a pear-shaped configuration of the device 1400 can be used to treat an aneurysm 1530 located at the tip of a basilar artery. In use, the device 1400 can be deployed across the bifurcation extending from one bifurcated vessel 1520 to the parent vessel 1500. Moreover, in alternative embodiments, a device for treating endovascular aneurysms consistent with the current disclosure can include any suitable variable outer diameter in order to achieve the same effect as shown with the pear-shaped configuration. In addition, all or part of the features of the pear-shaped configuration can be utilized with all or part of the features previously described above in connection with any of the devices described herein. Moreover, in yet alternative embodiments, a device for treating endovascular aneurysms consistent with the current disclosure can be controlled via the one or more elongated control members to achieve a variable outer diameter in order to achieve the same effect as shown with the pear-shaped configuration.

In a further embodiment consistent with the disclosure, any of the devices described herein can include a detachment mechanism configured to enable the expandable member to detach from the shaft and remain as a permanent support scaffold at the vessel. The detachment mechanism can be useful in circumstances where a physician is concerned about a prolonged embolization time inside the aneurysm. In addition, the detachment mechanism can serve as a safety feature in case coil herniation occurred during the procedure and cannot be resolved with the control wire (such as the one or more elongate control members). The detachment mechanism can be electrical, mechanical or chemical and can be configured to allow a physician to first determine the final dimensions of the expandable member (using a control filament or an elongated control member) and then detach the expandable member in its desired configuration. For example, in an embodiment consistent with the disclosure, an electric fuse can be located at a detachment connection point between the proximal end of the expandable member and the distal end of the shaft. The electric fuse can be configured to connect the one or more elongate control members to the expandable member, thereby attaching the expandable member to the shaft, and further can be configured to detach the expandable member from the shaft.

Figure 16:
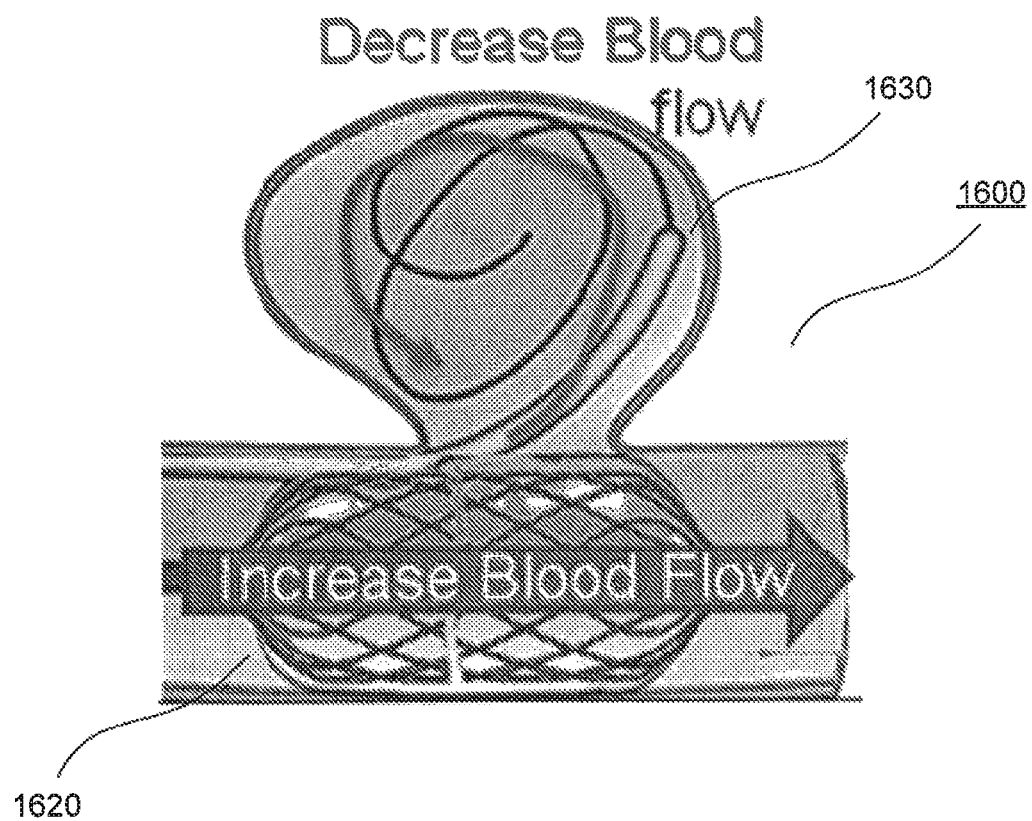
FIG. 16 is a perspective view of an embodiment consistent with the disclosure configured to divert blood flow away from an aneurysm.

Moreover, consistent with this disclosure and depicted in FIG. 16, a device 1600 can be configured as a temporary blood flow diverter. Diverting blood flow from an aneurysm sac 1630 into a parent vessel 1620 can be beneficial during endovascular aneurysm treatment, because it can accelerate blood coagulation inside the aneurysm. In an embodiment, diversion of blood flow can be accomplished by providing pulling force on an elongated control member in a manner than can decrease the size of the cells in the expandable member proximal to the aneurysm sac 1630. As a result, the device can impede the flow of blood to the aneurysm. In addition, the filaments of the expandable member can be coated to prevent local thrombosis and further mitigate the use of anticoagulant drugs.

Figure 19A:
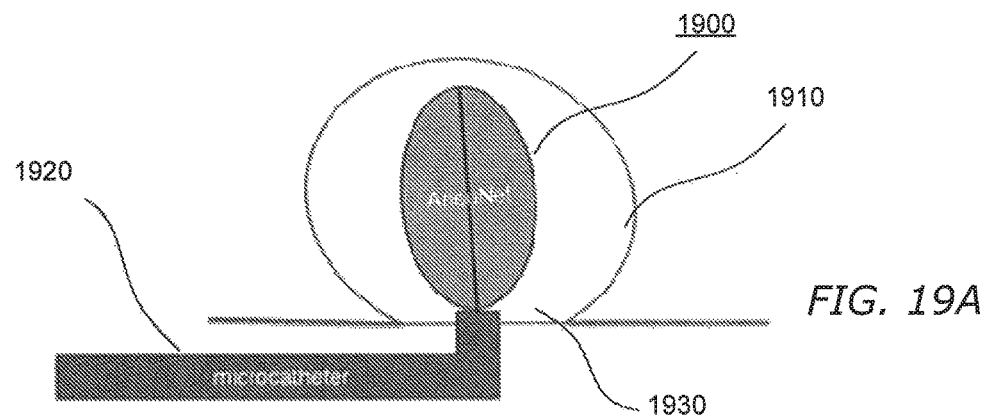
FIGS. 19A-C are perspective views illustrating aspects of a method of deploying a device consistent with the disclosure.

Consistent with the current disclosure, a device 1900 can also be configured to be deployed inside an aneurysm sac 1910, where the control filaments can be utilized to optimize opposition inside the sac. This is depicted in FIGS. 19A-9C. For example, in the same way that a detachable balloon can be deployed, the device 1900 can be unsheathed at the aneurysm 1910, and then expanded until an aneurysm neck 1930 is completely obstructed, and then the device 1900 can be detached (such as from a microcatheter 1920). This design does not require anti-coagulation therapy (on the contrary it is dependent on coagulation to succeed) and one size of device 1900 can be configured to fit many dimensions of the aneurysm 1910, allowing the physician to make any final adjustment in-situ.

Figure 19B:
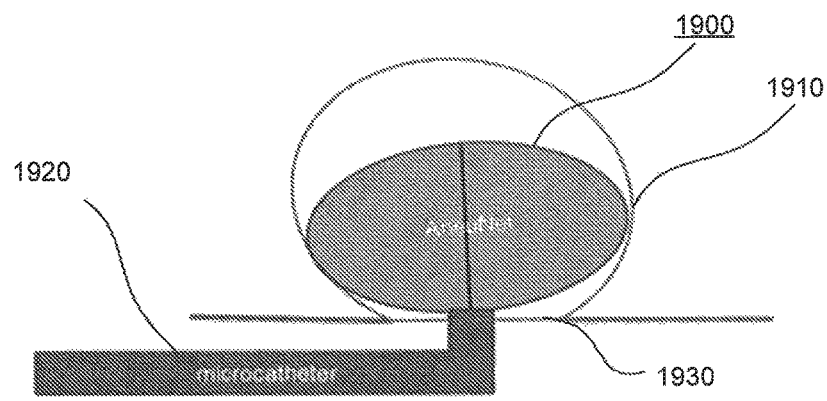
Figure 19C:
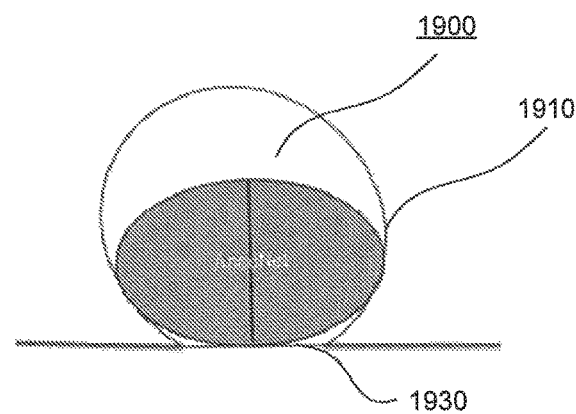

Embodiments of the any of the devices described herein can be used during various endovascular procedures. During these procedures, the user can control the usable length of the expandable member, its outer diameter, its cell size and its filament density. Further still, because the expandable member can be delivered to a target vessel through a microcatheter (such as microcatheter 1920 depicted in FIG. 19A and FIG. 19B), its practical length can be controlled by partial unsheathing. The outer diameter and cell size can also be controlled via the one or more elongated control members.

Figure 17:
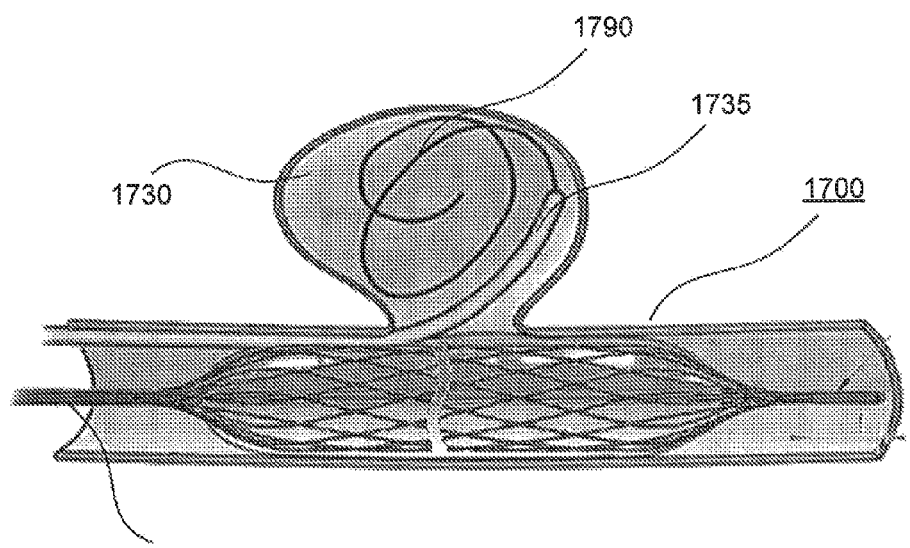
FIG. 17 is a perspective view depicting an embodiment consistent with the disclosure assisting intracranial aneurysm repair with coils.

Consistent with the disclosure herein, the device 1700 depicted in FIG. 17 can also be configured to support intracranial aneurysm repair with coils. A device operator can deliver two microcatheters to a target vessel, one microcatheter 1735 for delivering a coil 1790 (or coils) inside the aneurysm 1730 and the second microcatheter 1725 to deliver the device 1700. The coiling microcatheter 1735 can be normally placed ,inside the aneurysm 1730 and the device 1700 can be delivered and expanded in parallel to the coiling microcatheter 1735. This can cause the coiling microcatheter 1735 to be "jailed" inside the aneurysm 1730 and therefore provide a clinician with more control during the procedure. At the end of the procedure, the expandable member can be resheathed inside the microcatheter 1725 and then retrieved. The device 1700 can also be used during additional embolization techniques such as using liquids. Because the cell size adjacent to the aneurysm neck can be controlled with a control filament (such as an elongated control member), the cells can be adjusted to a size that is suitable for these alternative techniques.

Embodiments of a treatment device consistent with the disclosure can also be used for endovascular treatment of vasospasm. Similar to a balloon that is expanded at the vessel suffering from vasospasm, the elongated control members can be pulled to provide an available radial force on vessel walls (i.e., the elongated control members can be manipulated to exert the required radial force on the vessel). Because the device operator can have tactile feedback during the expansion of the device through the elongated control members (e.g. control filaments) and visual feedback if the device is radio-opaque, the device operator can decide on the amount of force to apply during the procedure.

Figure 18:
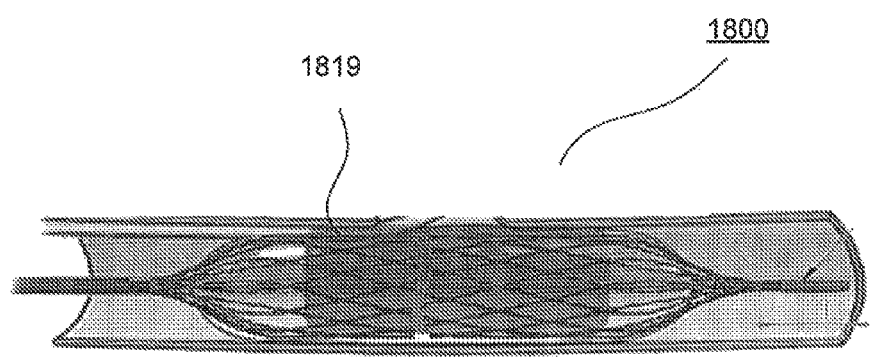
FIG. 18 is a perspective view depicting an embodiment consistent with the disclosure assisting a thrombectomy.

Furthermore, embodiments of a treatment device consistent with the disclosure can be used for thrombectomy. This embodiment is depicted in FIG. 18. In this case, it can be beneficial to control the amount of force exerted during the procedure combined with visual feedback on the actual dimensions of a device 1800 at the vessel. Device 1800 can be deployed adjacent or distally to the clot (similar to a "Stentriever") and then expanded as required. After deployment, the device 1800 can be retrieved in its expanded state. The physician can decide to expand the device 1800 even further during retrieval if the clot is pulled into vessels with a larger diameter.

Further still, a device consistent with the disclosure can be used to expand other endovascular devices (such as stents). It can be utilized in a similar way the balloon is used, using the control filaments (such as the elongated control members) to expand it when necessary and to retrieve at the end of the procedure.

It will be apparent to those skilled in the art that various modifications and variations can be made in the disclosed devices and methods without departing from the scope of the disclosure. That is, other embodiments will be apparent to those skilled in the art from consideration of the specification and practice of the embodiments disclosed therein. It is intended that the specification and embodiments be considered exemplary only, with a true scope of the invention being indicated by the following claims and their equivalents.

What is claimed:

1. An intravascular device, comprising:
an elongated shaft extending in an axial direction and being formed of a plurality of filaments, wherein the plurality of filaments of the elongated shaft are arranged in a single file continuum;
an expandable braided arrangement of the plurality of filaments, the braided arrangement having a proximal end, a distal end, and an intermediate region therebetween; and
a transition region of the plurality of filaments at an intersection of the elongated shaft and the braided arrangement, the plurality of filaments on one side of the transition region being oriented in a substantially parallel, non-crossing manner, and the plurality of filaments on an opposing side of the transition region crossing each other, and wherein the device is configured such that the plurality of filaments on an elongated shaft-side of the transition is substantially non-expandable and the plurality of filaments on a braided side of the transition is expandable.

2. The intravascular device of claim 1, further comprising a flexible cover surrounding the expandable braided arrangement.

3. The intravascular device of claim 1, further comprising a control member for permitting selective force application to the expandable braided arrangement in order to enable a selective variability in filament density.

4. The intravascular device of claim 3, wherein the filament density is variable between a liquid permeable density and a substantially liquid impermeable density.

5. The intravascular device of claim 1, wherein the plurality of filaments includes at least four filaments.

6. The intravascular device of claim 1, wherein the plurality of filaments includes at least six filaments.

7. The intravascular device of claim 1, wherein the plurality of filaments includes at least twelve filaments.

8. An intravascular device, comprising:
an expandable braided arrangement of a plurality of filaments, the braided arrangement having a proximal end, a distal end, and an intermediate region therebetween, and wherein the plurality of filaments in the intermediate region cross each other;
a coiled elongated shaft made up of the plurality of the filaments, wherein the plurality of filaments of the coiled elongated shaft are arranged in a single file continuum; and
a transition region between the proximal end of the expandable braided arrangement and the coiled elongated shaft, wherein in the transition region the plurality of filaments are bent to transition from a single file continuum on a shaft-side of the transition to a stacked orientation, and wherein on the braided side of the transition, the plurality of filaments cross each other and are arranged in an expandable manner, and on the coiled elongated side of the transition, the plurality of filaments are configured to be substantially non-expandable.

9. The intravascular device of claim 8, further comprising a flexible cover surrounding the expandable braided arrangement.

10. The intravascular device of claim 8, further comprising a control member for permitting selective force application to the expandable braided arrangement in order to enable a selective variability in filament density.

11. The intravascular device of claim 10, wherein the filament density is variable between a liquid permeable density and a substantially liquid impermeable density.

12. The intravascular device of claim 8, wherein the plurality of filaments includes at least four filaments.

13. The intravascular device of claim 8, wherein the plurality of filaments includes at least six filaments.

14. The intravascular device of claim 8, wherein the plurality of filaments includes at least twelve filaments.

* * * * *